United States Patent [19]

Daiss et al.

[11] Patent Number: 5,565,326
[45] Date of Patent: Oct. 15, 1996

[54] SEPARATION-FREE SPECIFIC BINDING ASSAYS USING ANTI-INHIBITOR ANTIBODIES

[75] Inventors: John L. Daiss; Kevin M. Gorman; Carolyn R. Hinchman, all of Rochester, N.Y.

[73] Assignee: Johnson & Johnson Clinical Diagnostics, Inc., Rochester, N.Y.

[21] Appl. No.: 250,883

[22] Filed: May 31, 1994

[51] Int. Cl.$^6$ .................................................. G01N 33/53
[52] U.S. Cl. .................. 435/7.71; 435/962; 435/969; 435/970; 435/975; 436/518; 436/523; 436/529; 436/530; 436/531; 436/548; 436/816; 436/822
[58] Field of Search .................. 422/56–58; 435/7.71, 435/12, 14, 15, 17, 21, 25, 28, 805, 962, 963, 968, 969, 970, 975; 436/518, 523, 529–531, 548, 808, 810, 815, 822, 816

[56] References Cited

U.S. PATENT DOCUMENTS

| | | | |
|---|---|---|---|
| 3,935,074 | 1/1976 | Rubenstein et al. | 435/7.9 |
| 4,161,515 | 7/1979 | Ullman | 424/8 |
| 4,233,401 | 11/1980 | Yoshida et al. | 435/7.9 |
| 4,430,263 | 2/1984 | Merch et al. | 435/7.71 |
| 4,621,048 | 11/1986 | Ashihara et al. | 435/5 |
| 4,686,181 | 8/1987 | Doná | 435/7.71 |

FOREIGN PATENT DOCUMENTS

| | | | |
|---|---|---|---|
| 0094777 | 11/1983 | European Pat. Off. | 435/7.71 |
| 0154276 | 11/1985 | European Pat. Off. | |
| 353614 | 2/1990 | European Pat. Off. | |
| 532187 | 3/1993 | European Pat. Off. | |
| 3227474 | 10/1983 | Germany. | |
| 8706006 | 8/1987 | WIPO. | |
| 90/07714 | 12/1988 | WIPO. | |
| 8908258 | 8/1989 | WIPO. | |
| 9007714 | 12/1990 | WIPO. | |

OTHER PUBLICATIONS

Henderson et al, *Clin. Chem.*, 32 (9), pp. 1637–1641 (1986).
Ngo, *int. J. Biochem.*, 15(5), pp. 583–590 (1983).
Derwent Abstract 92/176890/22, Syntex USA Inc, "Stabilizing conjugate of enzyme and specific binding pair—using antibody for enzyme in assays for analytes", EP 487301, see entire abstract.

*Primary Examiner*—Carol A. Spiegel

[57] ABSTRACT

Specific binding ligands can be detected with an assay which utilizes an immobilized receptor for the ligand, a reporter enzyme, an inhibitor antibody and an anti-inhibitor antibody. Both antibodies are specific for the reporter enzyme. The inhibitor antibody effectively shuts down the activity of the reporter enzyme when it is complexed thereto. The anti-inhibitor antibody binds to the reporter enzyme, does not affect the enzymatic activity, but prevents the binding of the inhibitor enzyme. This assay provides a direct correlation of the target specific binding ligand to the signal generated without the use of separation or wash steps.

20 Claims, 2 Drawing Sheets

SEPARATION-FREE SPECIFIC BINDING ASSAYS USING ANTI-INHIBITOR ANTIBODIES

FIELD OF THE INVENTION

This invention relates to a specific binding assay using antibodies specific to enzymes, which antibodies inhibit enzymatic activity. The assay also uses anti-inhibitor antibodies which are also specific to the same enzymes. This invention also relates to test kits and analytical elements useful in carrying out these assays. The invention has utility in diagnostics to detect various specific binding ligands which may be indicators of diseases.

BACKGROUND OF THE INVENTION

There is a continuing need in medical practice and research, and in analytical and diagnostic procedures, for rapid and accurate determinations of chemical and biological substances present in various fluids, such as biological fluids. For example, the presence of drugs, narcotics, hormones, proteins, toxins, microorganisms, viruses, steroids or nucleic acids must be rapidly and accurately detected for effective research, diagnosis or treatment of various diseases or conditions.

A wide variety of analytical methods have been developed in recent decades to detect chemical or biological substances. Most of such methods rely on what are known in the art as "specific binding" reactions in which an unknown substance to be detected (known as a "specific binding ligand") reacts specifically and preferentially with a corresponding "receptor" molecule. Most well known specific binding reactions occur between immunoreactants, such as antibodies and antigens, but other specific binding reactions (such as avidin with biotin, a sugar with a lectin or hormone with a receptor) are also known.

Many of the assay formats known in the art require one or more of the reactants to be immobilized on a solid substrate so that nonimmobilized reactants can be separated from immobilized reactants. Assays which require the presence of a solid phase for separation are generally known as "heterogeneous" and usually require a wash step.

In different assay formats which are known as "homogeneous", no separation step is generally needed because the desired signal can be detected in solution in the presence of all reactants. The elimination of wash or separation steps can be quite important in certain situations, such as in the use of dry analytical elements in automated equipment. Homogeneous assays have been commercialized and described in considerable literature, notably by Syva Corporation (for example, U.S. Pat. No. 3,935,074 of Rubenstein et al). In most homogeneous assays, an enzyme label is modulated in some fashion so that enzyme activity can be correlated to the amount of target specific binding ligand in a sample.

In homogeneous assays developed by Syva Corporation (EMIT™ assays), anti-ligand antibody partitions between free ligand and a conjugate of ligand and enzyme label. Anti-ligand antibody which binds to the conjugate reduces the catalytic activity of the enzyme. Despite its advantages, such assays have a primary limitation which is in the preparation of the conjugate. The enzyme commonly used in such assays (glucose dehydrogenase) has numerous substitution sites that are equally accessible, but only one of those sites is critical for the modulation of enzyme activity by the anti-ligand antibody. Thus, high substitution ratios are required to ensure that the majority of enzyme molecules are susceptible to inhibition. Different ligands alter the behavior of the resulting conjugate in terms of its solubility, retention of enzyme activity and susceptibility to inhibition. Variations in the conjugate may result from the manufacturing procedures, and thereby provide another cause for erratic assay performance. In other words, the known homogeneous assays are sensitive to small variations in concentration of the enzyme-ligand conjugate. In addition, the choice of enzyme labels is limited.

Another type of homogeneous assay, [Henderson et al, *Clin. Chem.*, 32(9), pages 1637–1641, (1986)], uses the assembly of a functional reporter enzyme (for example, β-galactosidase) from a pair of enzyme fragments, one of which is conjugated with target ligand. Anti-ligand antibody then interferes with assembly of the reporter enzyme by binding to the conjugate in the absence of target ligand. Two features make this assay difficult to carry out. The derivatization of the smaller enzyme fragment with target ligand can alter the assembly of functional enzyme or yield a conjugated fragment whose incorporation into functional enzyme is not blocked by anti-ligand antibody. Secondly, the equilibrium in the system of ligand, anti-ligand antibody and enzyme fragment conjugate lies near fully assembled enzyme and the resulting immunoassay is only transiently ligand dependent. That is, at equilibrium, the β-galactosidase will be fully active, independent of analyte. In other words, the assay is not kinetically robust.

There remains a need for an assay which is kinetically robust and uses reactants which are simple to manufacture with little variability. It would also be desirable to avoid separation steps which are common in heterogeneous assays.

SUMMARY OF THE INVENTION

The problems noted above have been solved with a separation-free specific binding assay comprising:

A) bringing together, in any order,
  1) a fluid sample suspected of containing a target specific binding ligand,
  2) an immobilized receptor for the target specific binding ligand,
  3) a reporter enzyme,
  4) an inhibitor antibody having the following characteristics:
    a) specific to the reporter enzyme,
    b) a dissociation constant less than or equal to about 125 nmolar, and
    c) binds to the reporter enzyme in such a manner as to inhibit the enzymatic activity of the reporter enzyme by at least about 80%, and
  5) a water-soluble conjugate of the target specific binding ligand and an anti-inhibitor antibody, the anti-inhibitor antibody having the following characteristics:
    a) specific to the reporter enzyme,
    b) a dissociation constant less than or equal to about 50 nmolar, and
    c) binds to the reporter enzyme in such a manner that the enzymatic activity of the reporter enzyme is diminished by no more than about 20% and binding of the inhibitor antibody with the reporter enzyme is substantially blocked,
  to form a complex between the immobilized receptor and either the target specific binding ligand or the water-soluble conjugate, and B) detecting any signal generated from the reporter enzyme as a determination of the target specific binding ligand in the fluid sample.

This invention also provides a test kit useful for a separation-free specific binding assay comprising, in individual packaging:

an immobilized receptor for a target specific binding ligand, and at least two additional reagents selected from the group consisting of:

a reporter enzyme, an inhibitor antibody having the following characteristics:
a) specific to the reporter enzyme,
b) a dissociation constant less than or equal to about 125 nmolar, and
c) binds to the reporter enzyme in such a manner as to inhibit the enzymatic activity of the reporter enzyme by at least about 80%, and a water-soluble conjugate of the target specific binding ligand and an anti-inhibitor antibody, the anti-inhibitor antibody having the following characteristics:
a) specific to the reporter enzyme,
b) a dissociation contant less than or equal to about 50 nmolar, and
c) binds to the reporter enzyme in such a manner that the enzymatic activity of the reporter enzyme is diminished by no more than about 20%, and binding of the inhibitor antibody with the reporter enzyme is substantially blocked.

Moreover, this invention also provides a dry analytical element comprising a porous spreading layer which contains an immobilized reporter enzyme, the element further comprising an immobilized receptor for a target specific binding ligand.

The assay of this invention is predicated on the mutually exclusive binding of two different antibodies which are both specific to a reporter enzyme which is used as a signal generating reagent in the system. One antibody (known herein as an "inhibitor" antibody) inhibits the enzymatic activity when it binds to the reporter enzyme. The other antibody (known herein as an "anti-inhibitor" antibody) binds to the reporter enzyme, but does not inhibit enzymatic activity to a significant extent. Yet, the anti-inhibitor antibody prevents the inhibitor antibody from binding to the reporter enzyme.

In the present invention, the activity of the reporter enzyme is directly proportional to the amount of target specific binding ligand in the assay system. A conjugate of anti-inhibitor antibody and the ligand is made to compete with ligand in the test sample for a limited number of receptor sites. In the absence of ligand, the conjugate will preferentially bind to the receptor sites, the inhibitor antibodies will have unrestricted access to the reporter enzyme, and the resulting enzyme activity will be low. In the presence of excess ligand, the conjugate will preferentially bind to the reporter enzyme and prevent the binding of the inhibitor antibody, thus allowing a high signal from the reporter enzyme.

Besides the advantage of avoiding separation steps, the present invention generates a fairly broad signal range and is not limited to analytes of 1000 daltons or less, as is common with conventional homogeneous immunoassays. The concentration of potential target specific binding ligands is generally in the range of nanomolar to millimolar. All of the reagents can be readily prepared using conventional methods. The reporter enzyme used to generate signal need not be immobilized or modified in any manner as is the case in homogeneous assays. In addition, this assay format should be useful with a wide variety of reporter enzymes.

DETAILED DESCRIPTION OF THE INVENTION

Figure 1:
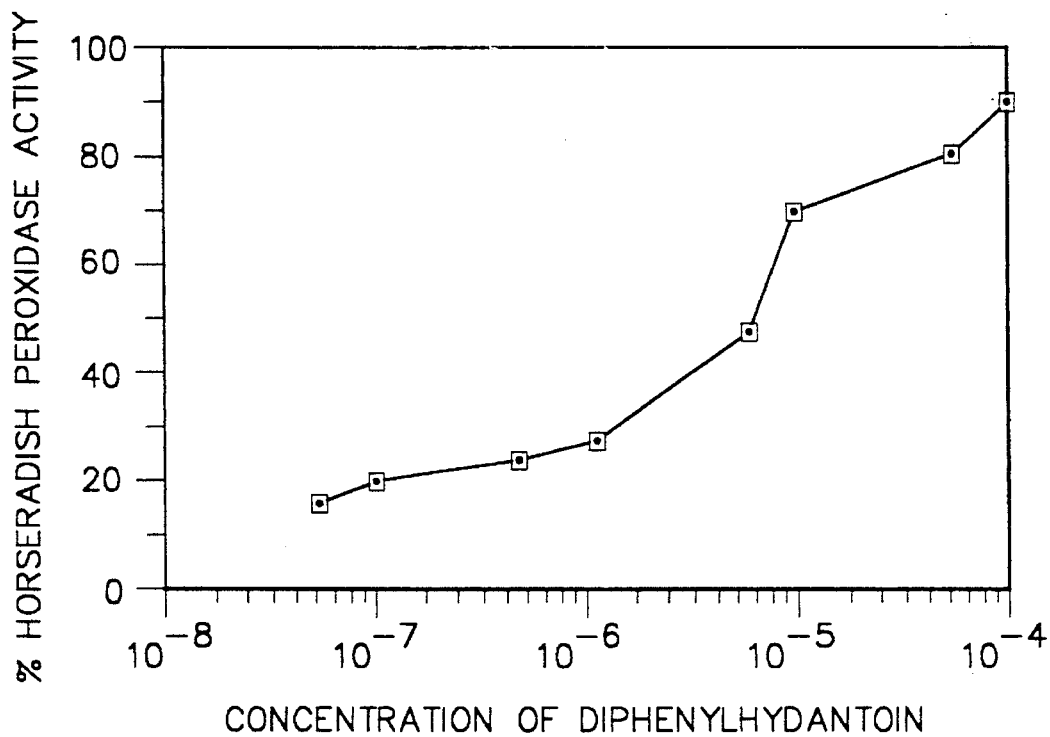
FIG. 1 is a graphical plot of observed % horseradish peroxidase activity vs. concentration of diphenylhydantoin, and is described in Example 1 below.

The present invention can be used to qualitatively, quantitatively or semi-quantitatively detect any of a wide variety of target specific binding ligands (identified as ligands hereinafter) for which receptor molecules are available or manufacturable. Examples of ligand-receptor complexes (that is, a reaction product of ligand and corresponding receptor) include, but are not limited to, antibody-antigen, antibody-hapten, avidin-biotin, sugar-lectin, gelatin-fibronectin and Protein A-IgG complexes. For the purposes of this invention, complementary nucleic acids (that is, hybridized products of complementary strands) are also considered ligand-receptor complexes. Such complementary nucleic acids need not be complementary at every base pair. One strand can be longer than the other, or one strand can have a plurality of shorter complementary strands.

Ligands include, but are not limited to, peptides, polypeptides, proteins (including enzymes, antibodies, antigenic proteins, glycoproteins, lipoproteins and avidin), hormones (such as human chorionic gonadotropin, thyroxine, triiodothyronine, estrogen, ACTH (adrenocorticotropic hormone) (and substance P), immune system modulators (such as interleukin-1, interleukin-6 and tumor necrosis factor $\alpha$), vitamins, steroids, carbohydrates (such as polysaccharides), glycolipids, therapeutic drugs and drugs of abuse (such as digoxin, diphenylhydantoin, phenobarbital, carbamazepine, morphine and theophylline), antibiotics (such as gentamicin), components of bacterial cells and viruses (such as Streptococcal species, herpes simplex virus, retroviruses, influenza viruses and Mycobacterium species), nucleic acids (including single- and double-stranded oligonucleotides), pharmaceuticals, haptens, lectins, biotin, and other materials readily apparent to one skilled in the art.

This invention is particularly useful for detecting drugs and hormones which are "low molecular weight", meaning less than about 1500 daltons, and including, but not limited to, those identified above, and most preferably for detecting drugs.

In preferred embodiments, the specific binding ligands are antigenic substances (such as the drugs noted above or haptenic analogs) or anti-antibodies.

In general, the separation-free assay protocol of this invention comprises bringing together the following reagents in any order:

1) the ligand (such as an antigenic substance) in a fluid sample of some type, 2) an immobilized receptor (such as an antibody) which is specific to and reactive with the ligand, 3) a reporter enzyme (described below), 4) an inhibitor antibody which is specific to the reporter enzyme and has additional properties defined below, and 5) a water-soluble conjugate of the ligand (such as a drug) and an anti-inhibitor antibody which is specific to the reporter enzyme and has additional properties as defined below.

While these reagents can be brought together in any order, it is preferred that the ligand (fluid sample), inhibitor antibody and conjugate be mixed with either the receptor or reporter enzyme before the remaining reagents are added. For example, the ligand, inhibitor antibody and conjugate can be mixed with the immobilized receptor, followed by addition of the reporter enzyme. Other sequences of bringing together the various reagents for this method would be readily apparent to one skilled in the art.

Once these reagents are brought together, appropriate reactions occur. Specifically, the ligand and water-soluble conjugate compete for available sites on the immobilized receptor. Signal is generated from the presence of the reporter enzyme in direct proportion to the amount of ligand in the fluid sample using appropriate signal generating reagents (described below). If there is no ligand present, the inhibitor antibody will complex with the reporter enzyme and inhibit its enzymatic activity, preventing signal generation. Signal is generated from the presence of active reporter enzyme only. In the presence of ligand which reacts with the immobilized receptor, the water-soluble conjugate will complex with the reporter enzyme and block the inhibitor antibody from reacting therewith, resulting in higher signal production from the reporter enzyme.

The reagents noted above can be brought together at suitable temperature, generally in the range of from about 4° to about 50° C., and preferably at room temperature. The time for mixing can vary from a few seconds to 15 minutes, although typically the mixing step requires about 1 to 5 minutes. Preferably, all of the reagents are mixed together substantially simultaneously in a suitable reaction vessel such as a microtiter plate. It is also preferred that the entire method be carried out within about 10 minutes.

The assay of this invention can be carried out in both "wet" or "dry" systems. That is, the assay can be carried out in the conventional "wet" system using suitable reaction containers whereby any generated signal is evaluated in the resulting reaction mixture. Alternatively and preferably, the assay is carried out in "dry" analytical elements (described below) in which the fluid sample is applied with or without additional fluids to dry test elements or test strips which may contain one or more additional reagents. Any generated signal is evaluated in the element itself either visually or using appropriate detection equipment.

The ligand to be detected may be present in any of a wide variety of fluid samples (or aqueous solutions) of animal or human body fluids including, but not limited to, whole blood, serum, plasma, lymph fluid, bile, urine, spinal fluid, lacrimal fluid, swab specimens, stool specimens, semen, vaginal secretions, saliva, tears, crevicular fluid, and others readily apparent to one skilled in the art. The size of the fluid sample can vary widely as is known in the art, but typically is at least about 10–100 μl.

The receptor is made available for reaction with the ligand or the ligand-anti-inhibitor antibody conjugate. Generally, such receptors are antibodies specific to the ligand.

The receptor is provided in immobilized form on a suitable water insoluble support. Suitable supports include, but are not limited to, polymeric, magnetic or glass particles, polymeric or glass filtration membranes, cellulosic filter papers, polymeric films, glass slides, test tubes, magnetic ferrofluids, test wells of test devices or microtiter plates, or other materials readily apparent to one skilled in the art. Preferably, the receptor is immobilized on polymeric particles designed for this purpose, which particles are well known in the art. Reactive groups on the surface of particles include, but are not limited to, carboxy, 2-substituted ethylsulfonyl, vinylsulfonyl, epoxy, aidehyde, active halo atoms, amino, hydrazine and active esters such as succinimidoxycarbonyl.

Particularly useful particulate supports are described, for example in EP-A-0 323 692 (published Jul. 12, 1989) and U.S. Pat. No. 4,997,772 (Sutton et al) which are prepared from one or more ethylenically unsaturated polymerizable monomers having active halo atoms, activated 2-substituted ethylsulfonyl or vinylsulfonyl groups. Particularly useful carboxy-containing polymeric particles are described in U.S. Pat. No. 5,262,297 (Sutton et al), incorporated herein by reference. Other carboxy-containing polymeric particles are described in the art and many are commercially available.

Attachment of the receptor to the support can be accomplished using any of a variety of conventional procedures, such as coating to adsorb the receptor molecules or incubating to allow covalent reaction with reactive groups on the support. Such procedures are described, for example, in U.S. Pat. No. 5,252,457 (Snodgrass et al) and U.S. Pat. No. 5,262,297 (Sutton et al), both incorporated herein by reference, and references cited therein. Most preferably, the receptor molecules are covalently attached to activated carboxy groups on polymeric particles, as described in the noted Sutton et al patent. The receptor can also be bound to supports having linking groups attached thereto, and such linking groups can be chemical moieties extending from the support or biological linking moieties such as peptides or antibodies to which the receptors can be complexed.

The amount of immobilized receptor useful in an assay would be readily apparent to a skilled worker from known assay protocols.

Reporter enzymes useful in this invention are enzymes which are typically used as labels in diagnostic systems. They include, but are not limited to a peroxidase, glucose oxidase, β-galactosidase, urease, alkaline phosphatase, creatine kinase, uricase, glucose-6-phosphate dehydrogenase and others readily apparent to one skilled in the art. A peroxidase (from any of various sources) is preferred, and horseradish peroxidase is most preferred.

The amount of reporter enzyme used in the assay is generally greater than or equal to about $10^{-11}$ molar so that background is negligible and kinetics for complex formation are acceptable. In addition, the amount is generally less than or equal to about $3 \times 10^{-8}$ molar so that enzyme substrates for producing signal are not reacted too quickly. Moreover, the amount is less than the concentration of either the inhibitor or anti-inhibitor antibodies (described below).

The reporter enzyme can be used in its "free" water-soluble form, or it can be immobilized on a suitable support, similar to the receptor molecules. Thus, the teaching above relating to supports for the receptor molecules applies equally for the reporter enzyme. For example, the reporter enzyme can be immobilized on suitable polymeric particles using procedures similar to those described above for attaching the receptor molecules to various supports. In particular, it is useful to immobilize the reporter enzyme using "binder" antibodies (described below) which are specific to the reporter enzyme and which are covalently attached to the particles.

As used herein for all antibodies (unless otherwise noted), the term "antibody" includes whole immunoglobulin molecules having the single specificity as is conventional in the art. In addition, the term is intended to include chemically prepared fragments [such as Fab, F(ab)', F(ab)'$_2$ fragments] of such molecules and genetically prepared equivalents thereof (such as "single chain antibody fragments" or ScFv fragments).

Each type of antibody described herein can be monoclonal or polyclonal (unless otherwise noted), but preferably, each type is monoclonal. Monoclonal antibodies include those molecules generally prepared using conventional hybridoma technology, but they can also be prepared by electrofusion, viral transformation and other procedures known in the art.

Preferably the monoclonal antibodies used in the practice of this invention are prepared by immunizing a suitable mammal (such as a mouse or rat) with the corresponding antigen, such as a reporter enzyme (or the reporter enzyme conjugated to carrier proteins), following the conventional procedures described by Kohler et al, *Nature* 256, 495 (1975). Details regarding specific procedures for preparing useful monoclonal antibodies are provided in copending and commonly assigned U.S. Ser. No. 08/251,496, filed on even date herewith by Gorman and Daiss and entitled "Inhibitor and Anti-Inhibitor Monoclonal Antibodies Specific for Horseradish Peroxidase".

A population of splenocytes from the immunized animals can be fused with suitable myeloma cell lines in the presence of polyethylene glycol (PEG1450) or another fusogen following the teaching of Lane [*J. Immunol. Methods* 81, pages 223–228 (1985)]. The resulting hybridized cells are diluted into selective media, distributed into microtiter plates and cultured for 7 to 21 days before screening to see what type of properties the antibodies possess. A specific procedure for preparing the antibodies is illustrated below.

A variety of myeloma cell lines are commercially available for hybridization with the mammalian spleen cells. Sources of such cell lines include the American Type Culture Collection (ATCC) in Rockville, Md. Particularly useful myeloma cell lines include Sp2/0-Ag14 and P3x63Ag8.653 myeloma cells, both available from the ATCC. The first cell line is preferred.

In the preparation of monoclonal antibodies for use in this invention, selected hybridomas were cloned in soft agar and individual clones were plucked, cultured using conventional means and screened using the procedures described above. Monoclonal antibodies can be grown in shaker flasks or hollow fiber bioreactors, and collected and purified using conventional affinity chromatography on either immobilized Protein A or Protein G. Other conventional purification procedures can be used if desired.

The inhibitor antibodies critical to the practice of this invention are specific to the reporter enzyme used in the assay. In addition, they have dissociation constants ($K_d$) less than or equal to about 125 nmolar, and bind to the reporter enzyme in such a manner as to inhibit the enzymatic activity of the reporter enzyme by at least about 80% (preferably by at least about 95%, and more preferably by at least about 99%). It should be understood that these $K_d$ values are relative measures for the antibodies, and that alternative methods for measuring that parameter may give higher or lower values.

Screening for antibody production is a critical step in hybridoma technology. The hybridoma culture supernatants described above can be screened by three independent assays. The first assay enables one to choose antibodies which are specific to the reporter enzyme, such as horseradish peroxidase. The second and third assays determine the inhibitory or anti-inhibitory properties of the specific antibodies determined in the first assay. Screening for horseradish peroxidase specificity is described below as illustrative of how such a screening process would be carried out for a given reporter enzyme, but this invention is not to be construed as so limited. It is believed that antibodies to other reporter enzymes could be similarly prepared and identified. Screening for specificity to the reporter enzyme can be readily accomplished using conventional Enzyme Linked Immunosorbent Assays (ELISA) in polystyrene microtiter plates containing adsorbed horseradish peroxidase conjugate.

Specificity for Horseradish Peroxidase

A sample (50 μl/plate well) of each culture supernate is placed in a microtiter well coated with a conjugate of horseradish peroxidase and an irrelevant antibody which served to mediate the adsorption of horseradish peroxidase to the microtiter plate. This antibody can be obtained, for example, from Jackson Immunoresearch. After a 30–60 minute incubation, the plates are washed with a suitable buffered solution of a nonionic surfactant, and the presence of mouse or rat horseradish peroxidase specific monoclonal antibodies is detected with a conjugate of anti-mouse IgG or anti-rat IgG and alkaline phosphatase (conjugate with anti-mouse Fc obtained, for example from Jackson Immunoresearch). A dye signal can be generated by adding the substrate o-nitrophenyl phosphate disodium salt (4 mg/ml) in tris(hydroxymethyl)aminomethane buffer (1.5 molar, pH 8). Other signal producing reagents, or enzyme labels can be similarly used. The screened antibodies which provide a dye signal after about 30 minutes which is at least twice as dense as a background signal are considered to be specific for horseradish peroxidase. The dye signal can be measured using a conventional microtiter plate reader or spectrophotometer.

Antibodies specific to horseradish peroxidase can be screened for inhibitory function as follows:

Assay for Enzyme Inhibition

A sample (50 μl) of each culture supernate is placed in a microtiter plate well, followed by addition of a solution (50 μl) of horseradish peroxidase (0.2 nmolar) and gelatin (0.8%) in phosphate buffered saline, and the resulting mixtures are allowed to stand for 10 minutes at room temperature. Residual enzyme activity is then determined by adding 100 μl of the horseradish peroxidase substrate, o-phenylenediamine (1 mg/ml), in citrate/phosphate buffer (50 mmolar, pH 5.5), and measuring the amount of dye signal at 450 nm using a conventional spectrophotometer (rate of 100 mOD/minute). Other substrates, or dye providing reagents can be similarly used.

Those culture supernates that inhibit horseradish peroxidase by more than about 20% (compared to a control without the presence of monoclonal antibody) are considered for further investigation as inhibitor antibodies.

The antibodies evaluated in this manner are subjected to further evaluation to find those which are within the scope of the present invention, namely those that inhibit the reporter enzyme (such as horseradish peroxidase) activity by at least about 80%. Preferably, the amount of inhibition is at least about 95%. The evaluation for inhibition was carried out by the procedure described above.

Antibodies specific to the reporter enzyme are also screened for their ability to inhibit the binding of inhibitor antibodies to the reporter enzyme. A representative screening process for anti-inhibitor antibodies specific to horseradish peroxidase is described below. This invention is not to be construed as so limited.

Assay for Anti-Inhibition

A sample (25 μl) of horseradish peroxidase (0.4 nmolar) is added to each well of a microtiter plate, followed by addition of a sample (50 μl) of each culture supernate, incubated 30 minutes, followed by addition of the inhibitor monoclonal antibody 4-22.2 (25 μl, 15 nmolar, defined below in Table I). After a 10 minute incubation, substrate solution (100 μl) is added and the dye signal from peroxidase activity is evaluated as described above (that is, using o-phenylenediamine as the substrate). Anti-inhibitor antibodies within the scope of this invention are defined as those which block the inhibition of horseradish peroxidase by the inhibitor antibody 4-22.2 described herein. Generally, the inhibitor antibody is added at a level sufficient to inhibit 80-90% of enzymatic activity, and more than 30% of the enzymatic activity is measured upon coincubation with an anti-inhibitor antibody.

When used to modify the percent of enzymatic activity inhibition in this disclosure and the claims, the term "about" refers to a variation of ±5%. When used to modify the $K_d$ values herein, the term "about" refers to a variation of ±50%.

The dissociation constants ($K_d$) for inhibitor antibodies were determined by measuring the concentration of the antibody required to inhibit 50% of the reporter enzyme (such as horseradish peroxidase) activity (as compared to enzymatic activity in the absence of antibody). The inhibitor antibodies described herein generally have a $K_d$ less than or equal to about 125 nmolar, preferably a $K_d$ less than or equal to about 50 nmolar, and more preferably a $K_d$ less than or equal to about 1 nmolar.

The $K_d$ values for anti-inhibitor antibodies were determined by measuring the concentration of antibody required to prevent 50% of the inhibition of 0.1 nmolar horseradish peroxidase by 10 nmolar of inhibitor antibody 4-22.2 (defined below in Table I) which was determined to inhibit about 99% of the enzymatic activity as defined above. These $K_d$ values are generally less than or equal to about 50 nmolar, preferably less than or equal to about 25 nmolar and more preferably less than or equal to about 5 nmolar. Preferably, these antibodies diminish the activity of horseradish peroxidase by no more than about 6%.

It should be understood that these $K_d$ values are relative measures for the antibodies, and that alternative methods for measuring that parameter may give higher or lower values.

The inhibitor, anti-inhibitor and binder monoclonal antibodies useful herein can be of any useful class, for example, IgA, IgE, IgM or IgG. Preferably, they are of the IgG class. Determination of isotype of cloned antibody cultures is achieved by using conventional isotyping assays and test kits which are commercially available. Reporter enzymes, such as horseradish peroxidase, can be immobilized on various supports, directly or indirectly, for isotyping assays.

The following Table I lists useful inhibitor monoclonal antibodies by species, isotype, $K_d$ and maximum horseradish peroxidase inhibition:

TABLE I

| Antibody | Species/Isotype | Kd (nmolar) | Max. Inhibition (%) |
| --- | --- | --- | --- |
| 4-22.2 | rat*/IgG1 | 0.14 | 99 |
| 3-8.1 | mouse**/IgG2a | 25 | 97 |
| 2-3.1 | mouse**/IgG1 | 2 | 85 |
| 3-7.2 | mouse**/IgG2a | 10 | 85 |
| 4-4.3 | rat*/IgG2a | 20 | 82 |
| 3-3.1 | mouse**/IgG1 | 50 | 93 |
| 3-6.2 | mouse**/IgG2a | 63 | 94 |
| 3-2.2 | mouse**/IgG2a | 110 | 91 |

*Sprague-Dawley rats
**Swiss/Webster mice

The 4-22.2 monoclonal antibody is preferred. It is prepared using the novel hybridoma cell line identified herein as HB11603 which has been deposited with the ATCC.

The following Table II lists useful anti-inhibitor monoclonal antibodies of this invention by species, isotype, $K_d$ and maximum horseradish peroxidase inhibition:

TABLE II

| Antibody | Species/Isotype | Kd (nmolar) | Max. Inhibition (%) |
| --- | --- | --- | --- |
| 7-32.2 | mouse**/IgG2a | 3.3 | 0 |
| 6-89.1 | rat*/IgG2a | 3.5 | 6 |
| 6-82.1 | rat*/IgG2a | 7.0 | 10 |
| 6-71.2 | rat*/IgG2a | 10 | 8 |
| 6-55.2 | rat*/IgG1 | 20 | 6 |

*Sprague-Dawley rats
**CAF$_1$ mice

The 7-32.2 monoclonal antibody is preferred. It is prepared using the novel hybridoma cell line identified herein as HB11604 which has been deposited with the ATCC under the Budapest Treaty. The 6-89.1 antibody is prepared using a novel hybridoma cell line identified herein as HB 11635 which has also been deposited with the ATCC under the Budapest Treaty.

The amount of inhibitor antibody used in the method of this invention is generally whatever amount is needed to inhibit enzyme activity at least about 80%. Generally, this is from about $10^{-9}$ to about $10^{-6}$ molar, with an amount of from about $10^{-9}$ to about $10^{-8}$ molar being preferred. The amount of inhibitor antibody will vary depending upon the level of inhibition of enzymatic activity that is desired, and the inhibition properties of a given antibody.

Also used in the method of this invention are water-soluble conjugates of the ligand and an anti-inhibitor antibody. The conjugates can be prepared using any conventional technique of the art for covalently binding proteins, hormones, drugs or other chemical or biological compounds having requisite reactive groups. Thus, the various reactive groups of the antibodies and ligand can be considered in choosing the means for making the conjugate, such groups including, but not limited to, carboxy, amino, hydroxy, thiol and imidazole groups. Useful methods of binding include, but are not limited to, binding of peptides, periodate oxidation, use of glutaraldehyde, dication ethers, carbamoylonium salts, carbodiimides or N-hydroxysuccinimide, and others readily apparent to one skilled in the art. Details for each of these and other methods are found in voluminous literature, including Williams et al *Method in Immunology and Immunochemistry*, Academic Press, New York, 1976, and Yoshitake et al, *Eur. J. Biochem.* 101, 395 (1979). It is to be understood that such conjugates are often prepared using derivatives or analogs (also known as haptens) of the ligand to be detected, such derivatives having reactive groups or linking moieties which may be desirable for binding the hapten to the reporter enzyme. Specific details of the preparation of several conjugates are provided below prior to the examples.

The amount of water-soluble conjugate used in the method of this invention is generally that amount needed to inhibit enzymatic activity by no more than about 20%, and to block substantially all reaction of inhibitor antibody with the reporter enzyme. By "substantially all" is meant at least 95%. Typically, the amount of conjugate is from about $4 \times 10^{-9}$ to about $2 \times 10^{-7}$ molar, with amounts of from about $10^{-8}$ to about $10^{-7}$ molar being preferred. The amount will vary depending upon properties of a given antibody, the amount of enzymatic activity desired and the amount of inhibitor antibody to be blocked.

Signal generated by the reporter enzyme in the course of the assay of this invention can be a chemiluminescent, electrochemical or colorimetric signal depending upon the particular reporter enzyme and corresponding reagents (such as substrates) used to generate the signal.

Chemiluminescent signals can be generated in a wide variety of ways in response to a reporter enzyme. In most chemiluminescent systems, the reporter enzyme is a peroxidase, and an oxidant such as hydrogen peroxide is present or generated in some fashion (for example, the reaction of an oxidase with its substrate). Useful chemiluminescent signals are generated using, for example, acridinium salts, tetrakis-(dimethylamino)ethylene, luciferin, lucigenin, oxalyl chloride, certain oxidases (for example, xanthine oxidase) and 2,3-dihydro-1,4-phthalazinediones (such as luminol and isoluminol). Many examples of such compounds and their uses are known in the art, for example, in U.S. Pat. No. 4,383,031 (Boguslaski et al), U.S. Pat. No. 4,598,044 (Kricka et al), U.S. Pat. No. 4,729,950 (Kricka et al), U.S. Pat. No. 5,108,893 (Baret) and *Chemiluminescence in Organic Chemistry* (Gundermann et al, Springer-Verlag, Berlin, 1987, pages 204–207). Where a chemiluminescent signal is generated, preferably peroxidase is used as the reporter enzyme, and luminol or a similar compound is used as a signal generating reagent.

Preferably, a colorimetric signal is generated in the method of this invention. Such signals can be achieved using a wide variety of reporter enzymes and reagents, as is well known in the art. Where the reporter enzyme is a peroxidase, as is preferred, useful dye-providing reagents include, but are not limited to, tetramethylbenzidine and derivatives thereof, o-phenylenediamine, triarylmethanes, and imidazole leuco dyes, such as the triarylimidazole leuco dyes described in U.S. Pat. No. 4,087,747 (Bruschi) and U.S. Pat. No. 5,024,935 (McClune), both incorporated herein by reference. Substrate solutions for the various reporter enzymes can be provided at any suitable time in the assay of this invention, or they can be present throughout the entire assay. One useful substrate solution for the triarylimidazole leuco dyes includes hydrogen peroxide, and an electron transfer agent such as 4'-hydroxyacetanilide or 3'-chloro-4'-hydroxyacetanilide in a suitable buffer.

The amount of various reagents needed to produce a desired signal would be readily apparent to one skilled in the art from consulting the voluminous literature available for the various signal producing systems. Specific enablement for a preferred colorimetric system is shown below in the examples.

The equipment needed for detecting the desired signal generated in the assay also would be readily apparent to one skilled in the art. Some colorimetric signals could be readily evaluated from the user's visual observations, but more generally, the signals are evaluated using appropriate apparatus for receiving and evaluating colorimetric, fluorimetric or chemiluminescent signals.

The reagents described herein and used in the practice of the method of this invention can be supplied as individually packaged components of a test kit. Such kits contain three or more of the necessary reagents, including an immobilized receptor as described above, and at least two additional reagents. The kits can also include suitable containers, equipment and instructions for carrying out the method of the invention, including test devices and filtration devices if needed. Preferably, the test kit includes all of the necessary reagents in individual containers.

The method of this invention can be carried out in suitable containers, such as microtiter plates, disposable test devices (such as those commercially available as SURCELL™ test devices), glass slides, test tubes and others readily apparent to one skilled in the art.

Preferably, the method can also be carried out using a dry analytical element of this invention which includes at least, an immobilized reporter enzyme, and the immobilized receptor as described above. The element comprises at least a porous spreading layer which can accommodate a test sample (generally from 1 to 200 μl), undiluted or undiluted, and can be in the form of filter papers, test slides, dipsticks and other configurations which would be readily apparent to one skilled in the art.

Preferably, the porous spreading layer is isotropically porous, which property is provided by interconnected spaces among the particles, fibers or other physical components of the porous spreading layer. By isotropically porous is meant that fluids are uniformly spread throughout the layer. Useful absorbent materials for such zones are water-insoluble and maintain their structural integrity during the assay. Conventional materials are described, for example, in U.S. Pat. No. 3,992,158 (Przybylowicz et al), U.S. Pat. No. 4,258,001 (Pierce et al), U.S. Pat. No. 4,292,272 (Kitajima et al) and U.S. Pat. No. 4,430,436 (Koyama et al), incorporated herein by reference. The preferred porous spreading layers are those prepared from organo-polymeric particles and a polymeric adhesive as described in the Pierce et al patent, and "blush" spreading layers as described in the Przybylowicz et al patent.

Preferably, the immobilized reporter enzyme is located in the porous spreading layer, and additional reagents are either added to the element during the assay or incorporated into separated layers, such as hydrophilic reagent layers over or beneath the porous spreading layer. All of the layers are preferably disposed on an inert, nonporous support prepared from a suitable material (such as a paper, metal foil, glass slide or polymeric film such as polyester, polycarbonate or polyolefin). The support may be transparent or not depending upon the mode of signal detection (for example, transmission or reflectance spectroscopy).

All of the additional layers are in "fluid contact" with the porous spreading layer, meaning that fluids and non-immobilized reagents can freely move among the layers. The binder materials typically used in such layers are well known in the art (such as gelatin, acrylamide polymers and vinylpyrrolidone polymers), such as the Pierce et al and Przybylowicz et al patents noted above. If desired, the elements can include one or more radiation blocking, subbing, or water-dissolvable layers as is known in the art.

The reporter enzyme and receptor used in the assay can generally be immobilized on distinct (or different) polymeric particles in the same or different layers of the element. In addition, the inhibitor antibody and water-soluble conjugate of ligand and anti-inhibitor antibody are incorporated into the element in suitable locations, provided that the antibodies and conjugate are kept separated from the immobilized receptor and immobilized reporter enzyme, but are available for reaction when a blood sample is added to the element. Such separation can be accomplished by putting the reagents in different layers of the elements, or some of the reagents can be encapsulated with water-dissolvable materials (such as gels, dextran or proteinoids) and kept in the same layer. When the test sample is added to the element, the encapsulating materials are dissolved releasing the reagents for reaction.

In a preferred embodiment of this invention, a multilayer element comprises a nonporous support having thereon, in fluid contact:

a first reagent layer, a subbing layer, and a porous spreading layer, the immobilized receptor and immobilized reporter enzyme located in the porous spreading layer, and the inhibitor antibodies and water-soluble conjugate of ligand and anti-inhibitor antibodies being in either the first reagent layer or subbing layer.

The elements can also include a variety of addenda in appropriate layers as are known in the art to aid in manufacture, fluid spreading, reagent stability and absorbance of unwanted background. The elements can be prepared using conventional coating procedures and equipment as are described in considerable art (including gravure, curtain, hopper and other coating techniques). The elements can be configured in a variety of forms, including elongated tapes of any desired width, sheets, slides or chips. Further, the method of the invention can be manual or automated to detect desired signal generated in the elements, using appropriate equipment and procedures. Generally, a test sample of fluid suspected of containing target specific binding ligand is spotted on the porous spreading layer, and the movement of fluid within the element effectively mixes the reagents for reaction.

After sample application, the element may be exposed to suitable conditioning, such as incubation, heating or other procedure, to quicken or facilitate the desired reactions within the element. Alternatively, the conditioning can be interrupted to add one or more reagents which are not incorporated into the element. The generated signal may be evaluated in a localized area of the element, or over its entire surface.

The following examples are illustrative of the invention and not meant to be limiting. All percentages are by weight, unless otherwise indicated.

Materials and Methods for Examples

Preparation of Inhibitor Monoclonal Antibody
Specific to Horseradish Peroxidase

The monoclonal antibody identified above as 4–22.2 in Table I above was prepared as follows:

Sprague-Dawley rats were injected with a solution of horseradish peroxidase (400 µg) in commercially available MPL®+TDM (trehalose dicorynomycolate+Monophosphoryl Lipid A Immunostimulant) emulsion adjuvant (RIBI Corporation) four times at four week intervals. A fifth injection was made with horseradish peroxidase (400 µg) in phosphate buffered saline solution. Three days later, splenocytes from the immunized rats were fused with cells from the Sp2/0-Ag14 myeloma cell line using conventional procedures.

Screening of the resulting antibodies for specificity to horseradish peroxidase was carried out as described above by adding 50 µl of the culture supernatant to the wells of a microtiter plate coated with a conjugate of horseradish peroxidase and irrelevant antibody which served to mediate the adsorption of the enzyme to the microtiter plate. The bound antibody was detected by adding a conjugate of alkaline phosphatase with goat anti-mouse IgG Fc (Jackson Immunoresearch), following by signal generation using 4 mg/ml of p-nitrophenyl phosphate disodium salt (Sigma Chemical) as substrate for the alkaline phosphatase in tris(hydroxymethyl)aminomethane buffer (1.5 molar, pH 8). The dye signal was evaluated after 30 minutes using a conventional microtiter plate reader.

Screening for horseradish peroxidase inhibitory function was carried out by adding a sample (50 µl) of each culture supernatant to microtiter plate wells, followed by addition of horseradish peroxidase (0.2 nmolar) and gelatin (0.8%) in phosphate buffered saline solution, and the resulting mixtures were allowed to incubate for 10 minutes at room temperature. Residual horseradish peroxidase activity was determined by adding a solution (100 µl) of o-phenylenediamine (1 mg/ml) in citrate/phosphate buffer (50 µl, 50 mmolar, pH 5.5), and measuring the amount of dye signal at 450 nm using a conventional microtiter plate reader (100 mOD/minute).

Those antibodies which inhibited the enzymatic activity by at least 20% were selected by adding equal volumes of the culture supernatant and horseradish peroxidase to microtiter plate wells and using the procedure described above ("Assay for Enzyme Inhibition"). Antibody 4–22.2 was determined to inhibit horseradish peroxidase activity 99%.

Preparation of Anti-Inhibitor Monoclonal Antibody
Specific to Horseradish Peroxidase The monoclonal antibody identified above as 7–32.2 in Table II was prepared as follows:

Immunization of mice and fusion of the resulting splenocytes were carried out as described above in the previous preparation. Mice were given four immunizations of a conjugate (100 µg/ml each) of horseradish peroxidase with C-reactive protein in TDM/MPL emulsion adjuvant over four week intervals. A fifth and final immunization in phosphate buffered saline solution was carried out. Screening for horseradish peroxidase activity was carried out as described above except that after the plates were shaken for 10–30 minutes, a solution (25 µl) of the inhibitor antibody 4–22.2 (about 15 nmolar, described above) was added to each plate well. The resulting mixtures were allowed to incubate for 10 minutes at room temperature.

Residual horseradish peroxidase activity was determined by adding a solution (100 µl) of o-phenylenediamine (1.2 mg/ml) in citrate/phosphate buffer (0.1 molar, pH 5.5), and measuring the amount of dye signal at 450 nm using a conventional spectrophotometer as described in the previous preparation.

The determination of an antibody which is an anti-inhibitor was carried out using the procedure described above ("Assay for Anti-Inhibition"). Antibody 7–32.2 was measured to diminish enzyme activity by less than 1% (essentially 0%).

Preparation of Conjugates of Anti-Inhibitor Monoclonal Antibody and Diphenylhydatonin Hapten Water-soluble conjugates of a diphenylhydantoin hapten and two anti-inhibitor monoclonal antibodies were prepared. This preparation is representative only, and is not essential to preparing conjugates useful in the present invention. Alternative preparatory methods also exist.

The hapten, 5,5-diphenyl-3-{4-[4-(3-succinimidoxycarbonylpropionyl)-1-piperazinylcarbonyl]butyl}-2,4-imidazolidinedione, was prepared by procedures described in Preparatory Example 2 of EP-A-0 517 327 (published May 5, 1993).

This hapten was conjugated to the monoclonal antibodies identified as 7–32.2 or 6–89.1 (Table II) in either a 9:1 or 18:1 molar ratio by adding concentrated hapten in dimethyl sulfoxide slowly, dropwise to a solution of either antibody (1 mg/ml) in N-[2-hydroxyethyl] piperizine-N'-[3-propanesulfonic acid] buffer (0.1 molar, pH 8). The resulting mixtures were incubated at room temperature for 4 hours, then dialyzed overnight into phosphate buffered saline solution. The final product conjugates were filtered through a commercially available 0.22 µmeter filter (Nalge Corporation, Rochester, N.Y.). The final protein concentration was determined by absorbance at 280 nm using a commercially available spectrophotometer (Beckman Instruments).

Preparation of Conjugates of Anti-Inhibitor Monoclonal Antibody and Phenobarbital Hapten Two water-soluble conjugates of a phenobarbital hapten and anti-inhibitor monoclonal antibodies were prepared in the following manner. This preparation is representative only, and is not essential to preparing conjugates useful in the present invention. Alternative preparatory methods also exist.

The hapten, 5-ethyl-5-phenyl-1-{4-[4-(3-succinimidoxycarbonylpropionyl)-1-piperazinylcarbonyl]-butyl)-2,4,6-(1H,3H,5H)pyrimidinetrione, was prepared by procedures described in Preparatory Example 4 of EP-A-0 517 327 (published May 5, 1993).

This hapten was conjugated to the monoclonal antibodies identified as 7–32.2 or 6–89.1 (Table II) in either a 9:1, 18:1 or 27:1 molar ratio by adding concentrated hapten in dimethyl sulfoxide slowly, dropwise to a solution of antibody (1 mg/ml) in N-[2-hydroxyethyl]piperizine-N'-[3-propanesulfonic acid] buffer (0.1 molar, pH 8). The resulting mixtures were incubated at room temperature for 4 hours, then dialyzed overnight into phosphate buffered saline solution. The final product conjugates were filtered through a commercially available 0.22 µmeter filter (Nalge Corporation, Rochester, N.Y.). The final protein concentration was determined by absorbance at 280 nm using a commercially available spectrophotometer (Beckman Instruments).

Preparation of Conjuaates of Anti-Inhibitor Monoclonal Antibody and Digoxin Hapten Two water-soluble conjugates of a digoxin hapten and anti-inhibitor monoclonal antibodies was prepared in the following manner. This preparation is representative, as other methods for making such conjugates can be used.

Hapten was conjugated to the monoclonal antibodies identified as 7–32.2 or 6–89.1 (Table II) by diluting 2 mg of each antibody 1:1 with sodium acetate (0.1 molar, pH 5.5), not to exceed 2 ml. Sodium metaperiodate (1 ml) was added at 6.66 mg/ml. The reaction mixture was covered with foil and rotated for 20 minutes at room temperature. Excess sodium metaperiodate was removed by passing the reaction mixture over a commercially available PD10 column (Pharmacia, Inc.) and preequilibrated with sodium acetate (0.1 molar, pH 5.5). Two vials (3 mg in 1 ml) of digoxigenin-x-hydrazide (Boehringer Mannheim) were added to each mixture and incubated for 1 hour at room temperature. To block reaction, excess glycine (final concentration of 10%) was added at pH 7, followed by sodium cyanoborohydride in water to a final concentration of 20 mmolar. The reaction mixture was stirred for 3 hours at room temperature, then dialyzed overnight into 3-(N-morpholino)propanesulfonic acid (0.02 molar, pH 7) buffer. The final product conjugates were filtered through a commercially available 0.22 µmeter filter (Nalge Corporation, Rochester, N.Y.). The final protein concentration was determined by absorbance at 280 nm using a commercially available spectrophotometer (Beckman Instruments).

Immobilization of Antibodies

Antibodies to various target specific binding ligands used in the assays of the examples were immobilized on particles of poly[styrene-co-3-(p-vinylbenzylthio)propionic acid] (molar ratio of 95:5, 1 µm average size) using the procedures described in U.S. Pat. No. 5,177,023 (Sutton et al), incorporated herein by reference. Antibodies specific to diphenylhydantoin were obtained from Beckman.

Antibodies specific to horseradish peroxidase which inhibit neither its enzymatic activity, nor the binding of inhibitor antibodies to the enzyme were also prepared and used in the practice of this invention. These antibodies are identified herein as "binder" antibodies because they specifically bind to horseradish peroxidase. However, they do not have the properties of the inhibitor or anti-inhibitor antibodies described herein, to a substantial extent. The binder antibodies were prepared and identified using the conventional hybridoma technology described above, and the screening process described above. Such antibodies exhibited high affinity for the enzyme. Once such antibody is identified herein as "5–10" and is an IgG1 antibody derived using the procedures described above using Balb/c. Its $K_d$ was determined to be at least $10^{-8}$ and its inhibition of horseradish peroxidase was less than 1%.

Horseradish peroxidase, isoenzyme C was obtained from Servac, Inc. (South Africa). It was immobilized on the same type of polymeric particles described above for the anti-ligand antibodies by complexing it with binder antibody 5–10 which had been immobilized using the procedures described in U.S. Pat. No. 5,177,023 (noted above).

Enzyme substrate solution A contained o-phenylenediamine (30 mg) in a solution (25 ml) of citrate buffer (0.05 molar sodium citrate, 0.1 molar sodium pohsphate dibasic, pH 5.5) containing merthiolate (0.1%). In the final product (per 1.33 liter), a one gram table of urea/hydrogen peroxide was added.

Enzyme substrate solution B was prepared by adding a solution (5 ml) of 4,5-bis(4-dimethylamino-phenyl)-2-(4-hydroxy-3-methoxyphenyl)imidazole leuco dye (1 g) in N,N-dimethylformamide to a solution (500 ml) of polyvinylpyrrolidone (125 g) and stirred for an hour. Diethylenetriamidepentaacetic acid (1 ml, 0.1 molar) was added to a solution (9500 ml) of monobasic sodium phosphate monohydrate (13.8 g) with stirring, followed by addition of 3'-chloro-4'-hydroxyacetanilide (9.4 g). The resulting mixture was stirred to dissolve the components, and the pH was adjusted to 6.8 with 50% sodium hydroxide. With vigorous stirring, it was then mixed with the leuco dye solution. Hydrogen peroxide (10 ml, 30%) was added, and the final mixture was stirred another 15 minutes.

EXAMPLE 1

Separation-Free Assay for Diphenylhydatoin

The ligand diphenylhydantoin (phenytoin) was determined according to the present invention as follows:

Inhibitor antibody solution ($10^{-9}$ molar) and anti-inhibitor antibody-diphenylhydantoin conjugate solution ($5.3 \times 10^{-8}$ molar) were mixed (25 μl total volume). To this mixture was added a test sample (25 μl) containing diphenylhydantoin (various concentrations of 0 to $10^{-4}$ molar) and gelatin (0.8%) in phosphate buffered saline solution. A suspension of horseradish peroxidase attached to polymeric particles, as described above (25 μl, $10^{-10}$ molar), and anti-diphenylhydantoin antibodies attached to polymeric particles, as described above (25 μl, $3 \times 10^{-6}$ molar), was prepared. This suspension was then mixed with the mixture containing analyte to form a reaction mixture (100 μl, pH 7), and placed in the well of a conventional microtiter plate. The mixture was incubated at room temperature with agitation for 10 minutes, after which the enzyme substrate solution of o-phenylenediamine (100 μl) was added with further mixing on a plate shaker. The dye signal from the enzyme activity was measured using a TITERTEK™ MCC340 Mark II commercially available microtiter plate reader at 450 nm.

The resulting dose response curve is shown in FIG. 1 with % horseradish peroxidase activity on the y-axis and molar concentration of diphenylhydantoin on the x-axis. It is apparent that increasing amounts of ligand in the various test samples were directly correlated to the increasing amount of enzyme activity observed in the immunoassay. The rate of enzymatic activity observed was about 10% of the uninhibited rate at the lower ligand concentrations, and was as high as 60% of the uninhibited rate at the higher ligand concentration.

EXAMPLE 2

Separation-Free Assay for Phenobarbital

The ligand phenobarbital was determined according to the present invention as follows:

Inhibitor antibody solution ($10^{-9}$ molar) and anti-inhibitor antibody-phenobarbital conjugate solution ($5.3 \times 10^{-8}$ molar) were mixed (25 μl total volume). To this mixture was added a test sample (25 μl) containing phenobarbital (various concentrations of 0 to $10^{-4}$ molar) and gelatin (0.8%) in phosphate buffered saline solution. A suspension of horseradish peroxidase attached to polymeric particles, as described above (25 μl, $10^{-10}$ molar), and antiphenobarbital antibodies attached to polymeric particles, as described above (25 μl, $3 \times 10^{-6}$ molar), was prepared. This suspension was then mixed with the mixture containing analyte to form a reaction mixture (100 μl, pH 7), and placed in the well of a conventional microtiter plate. The mixture was incubated at room temperature with agitation for 5 minutes, after which the enzyme substrate solution of o-phenylenediamine (100 μl) was added with further mixing on a plate shaker. The dye signal from the enzyme activity was measured using a TITERTEK™ MCC340 Mark II commercially available microtiter plate reader at 450 nm.

Figure 2:
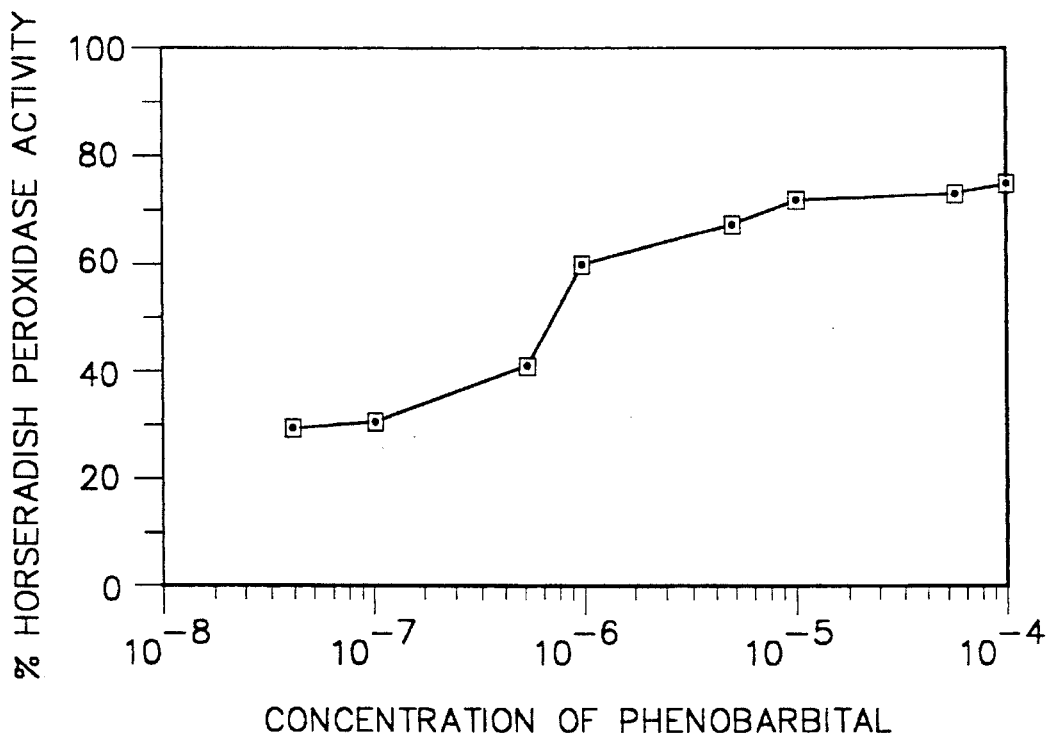
FIG. 2 is a graphical plot of observed % horseradish peroxidase activity vs. concentration of phenobarbital, and is described in Example 2 below.

The resulting dose response curve is shown in FIG. 2 with % horseradish peroxidase activity on the y-axis and molar concentration of phenobarbital on the x-axis. It is apparent that increasing amounts of ligand in the various test samples were directly correlated to the increasing amount of enzyme activity observed in the immunoassay. The rate of enzymatic activity observed was about 28% of the uninhibited rate at the lower ligand concentrations, and was as high as 75% of the uninhibited rate at the higher ligand concentration. The mid-point of the curve was at about $10^{-6}$ molar.

EXAMPLE 3

Separation-Free Assay for Digoxin

The ligand digoxin was determined according to the present invention as follows:

Inhibitor antibody solution ($10^{-9}$ molar) and anti-inhibitor antibody-digoxin conjugate solution ($5.3 \times 10^{-8}$ molar) were mixed (25 μl total volume). To this mixture was added a test sample (25 μl) containing digoxin (various concentrations of 0 to $10^{-4}$ molar) and gelatin (0.8%) in phosphate buffered saline solution. A suspension of horseradish peroxidase attached to polymeric particles, as described above (25 μl, $10^{-4}$ molar), and anti-digoxin antibodies attached to polymeric particles, as described above (25 μl, $3 \times 10^{-6}$ molar), was prepared. This suspension was then mixed with the mixture containing analyte to form a reaction mixture (100 μl, pH 7), and placed in the well of a conventional microtiter plate. The mixture was incubated at room temperature with mixing for 15 minutes, after which the enzyme substrate solution of o-phenylenediamine (100 μl) was added with further mixing on a plate shaker. The dye signal from the enzyme activity was measured using a TITERTEK™ MCC340 Mark II commercially available microtiter plate reader at 450 nm.

Figure 3:
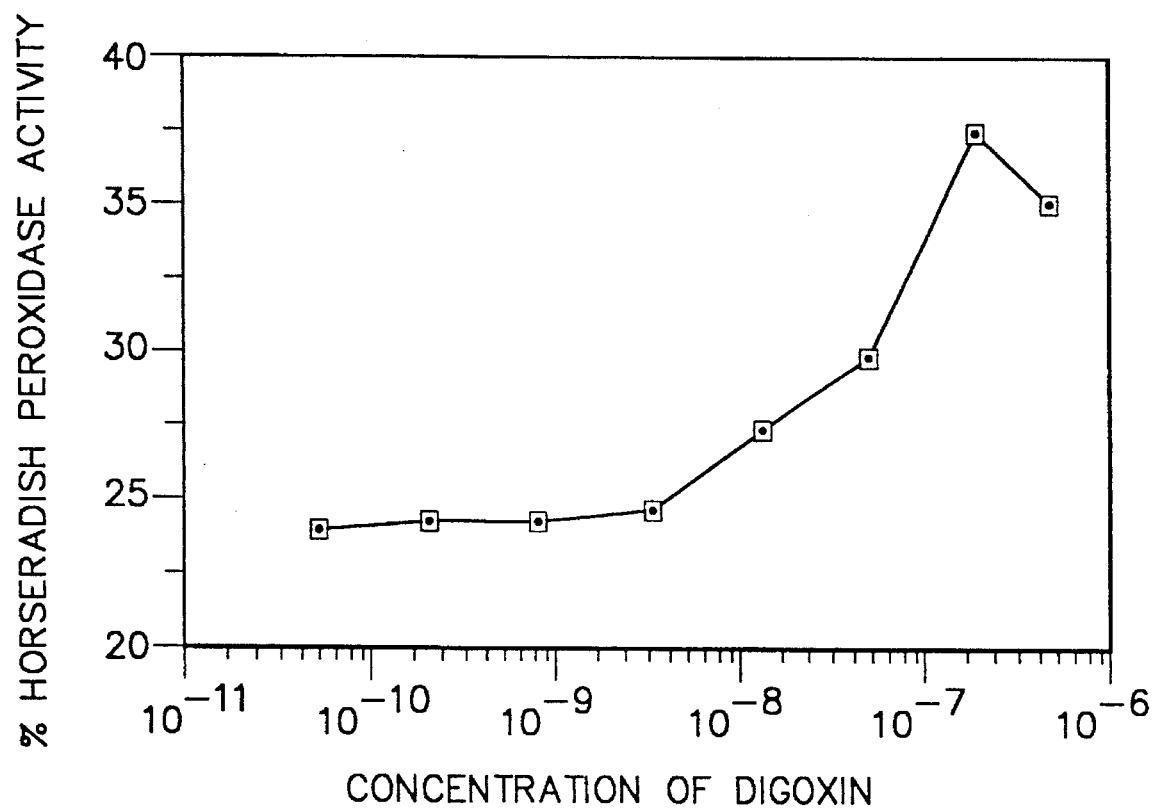
FIG. 3 is a graphical plot of observed % horseradish peroxidase activity vs. concentration of digoxin, and is described in Example 3 below.

The resulting dose response curve is shown in FIG. 3 with % enzyme activity on the y-axis and molar concentration of digoxin on the x-axis. It is apparent that increasing amounts of ligand in the various test samples were directly correlated to the increasing amount of enzyme activity observed in the immunoassay. The rate of enzymatic activity observed was about 23% of the uninhibited rate at the low ligand concentrations, and was as high as 36% of the uninhibited rate at the high ligand concentration, which means this assay was not optimized. The midpoint of the curve was at about $3 \times 10^{-7}$ molar.

EXAMPLE 4

Analytical Element Useful for Homogeneous Assay for Diphenylhydatoin

An element of this invention useful for the detection of diphenylhydantoin was prepared having the following layer arrangement and components:

| ELEMENT STRUCTURE | | |
|---|---|---|
| Layer | Material | Coverage (g/m$^2$) |
| Spreading Layer | Poly(vinyltoluene-co-methacrylic acid) (98:2 weight ratio) beads | 130.0 |
| | Poly(methyl acrylate-co-sodium 2-acrylamido-2-methylpropane-sulfonate-co-2-acetoacetoxyethyl methacrylate) (90:4:6 wt. ratio) | 2.583 |

-continued

ELEMENT STRUCTURE

| Layer | Material | Coverage (g/m$^2$) |
|---|---|---|
| | Bovine serum albumin | 1.00 |
| | Glycerol | 2.00 |
| | Mannitol | 1.00 |
| | Dimedone | 0.50 |
| | Dimethyl sulfoxide | 1.80 |
| | 4,5-bis(4-dimethylaminophenyl)-2-(3,5-dimethoxy-4-hydroxy-phenyl)imidazole leuco dye | 0.20 |
| | 4'-Hydroxyacetanilide | 0.45 |
| | N-[Tris(hydroxymethyl)methyl-2-aminoethanesulfonic acid buffer) | 0.219 |
| | Immobilized anti-diphenylhydantoin monoclonal antibodies | 2.4 |
| | Horseradish peroxidase immobilized on polymer particles using binder antibodies 5–10 | 0.25 |
| Binder Layer | Gelatin (hardened) | 10.00 |
| | Bis(vinylsulfonyl methyl) ether | 0.15 |
| | 4'-Hydroxyacetanilide | 0.15 |
| | TRITON ™ X-100 nonionic surfactant | 0.02 |
| | N-[Tris(hydroxymethyl)methyl-2-aminoethanesulfonic acid buffer | 4.58 |
| | Poly(ethylene terephthalate) Support | |

Several samples of the element were evaluated using the following solutions:

1) No analyte or 10$^{-4}$ molar diphenylhydantoin.

2) Either 10 or 3.16 µg/ml inhibitor antibody 4–22.2.

3) Water-soluble anti-inhibitor antibody-diphenylhydantoin conjugate at 0.8, 2.5, 8 or 25 µg/ml.

The assays were carried out by spotting 10 µl of each of the three solutions noted above onto the element spreading layer and incubating at room temperature for 5 minutes. A substrate solution (10 µl) containing hydrogen peroxide, diethylenetriaminetetrapentaacetic acid (10 µmolar), 4'-hydroxyacetanilide (5 mmolar) in sodium phosphate dibasic (10 mmolar, pH adjusted to 6.8 with sodium hydroxide) was then applied, and after 15 minutes, the dye signals in each element were evaluated by taking a photographic image of each element using conventional KODAK GOLD™ 200 color print film. Dye signal was visually assessed as followed:

− No dye signal

+ Some dye signal

++++ Considerable dye signal

The results are listed in the following Table III.

TABLE III

| Anti-inhibitor Conjugate Concentration (µg/ml) | Inhibitor Antibody Concentration | | | |
|---|---|---|---|---|
| | 10 µg/ml | | 3.16 µg/ml | |
| | Analyte Concentration | | | |
| | 0 | 10$^{-4}$ molar | 0 | 10$^{-4}$ molar |
| 0.8 | − | − | − | + |
| 2.5 | − | + | + | ++ |
| 8 | + | ++ | ++ | +++ |
| 25 | ++ | ++++ | ++½ | ++++ |

The invention has been described in detail with particular reference to preferred embodiments thereof, but it will be understood that variations and modifications can be effected within the spirit and scope of the invention.

We claim:

1. A separation-free specific binding assay comprising:
   A) contacting together, in any order,
      1) a fluid sample suspected of containing a target specific binding ligand,
      2) an immobilized receptor for said target specific binding ligand,
      3) a reporter enzyme,
      4) an inhibitor antibody having the following characteristics:
         a) specifically binds to said reporter enzyme,
         b) a dissociation constant less than or equal to about 125 nmolar, and
         c) specifically binds to said reporter enzyme in such a manner as to inhibit the enzymatic activity of said reporter enzyme by at least about 80%, and
      5) a water soluble conjugate of said target specific binding ligand and an anti-inhibitor antibody having the following characteristics:
         a) specifically binds to said reporter enzyme,
         b) a dissociation constant less than or equal to about 50 nmolar, and
         c) specifically binds to said reporter enzyme in such a manner that the enzymatic activity of said reporter enzyme is diminished by no more than 20%, and wherein said anti-inhibitor antibody prevents said inhibitor antibody from binding with said reporter enzyme,
   to form a reaction mixture comprising a complex between said immobilized receptor and either said target specific binding ligand or said water-soluble conjugate,
   B) contacting said reaction mixture simultaneously or sequentially with a signal-generating reagent comprising a substrate for the reporter enzyme, and
   C) detecting any signal generated from said reporter enzyme as a determination of said target specific binding ligand in said fluid sample.

2. The method of claim 1 wherein said reporter enzyme is immobilized on a water-insoluble support.

3. The method of claim 2 wherein said reporter enzyme is immobilized on polymeric particles and wherein said receptor is immobilized on polymeric particles.

4. The method of claim 1 wherein either or both of said inhibitor antibody and said anti-inhibitor antibody are monoclonal antibodies.

5. The method of claim 1 wherein said reporter enzyme is a peroxidase, alkaline phosphatase, creatine kinase, glucose oxidase, urease, glucose-6-phosphate dehydrogenase or beta-galactosidase.

6. The method of claim 1 wherein said reporter enzyme is horseradish peroxidase.

7. The method of claim 1 wherein:
   said inhibitor antibody is monoclonal, has a dissociation constant of less than or equal to about 10 nmolar, and binds to said reporter enzyme in such a manner as to inhibit at least about 95% of the enzymatic activity of said reporter enzyme, and
   said anti-inhibitor antibody is monoclonal, has a dissociation constant less than or equal to about 5 nmolar, and binds to said reporter enzyme in such a manner that the enzymatic activity of said reporter enzyme is diminished by no more than about 6%.

8. The method of claim 1 wherein said substrate is a chromogenic substrate and said detecting comprises measuring colored product.

9. The method of claim 1 wherein said target specific binding ligand is diphenylhydantoin, digoxin or phenobarbital; wherein said immobilized receptor is an antibody which specifically binds thereto; and wherein said water-soluble conjugate is formed from said anti-inhibitor antibody and said target specific binding ligand.

10. The method of claim 1 wherein said fluid sample, said inhibitor antibody and said water-soluble conjugate are contacted together prior to contact with said immobilized receptor or said reporter enzyme.

11. A test kit useful for a separation-free specific binding assay comprising, in individual packaging:

an immobilized receptor for a target specific binding ligand, and at least two additional reagents selected from the group consisting of:

a reporter enzyme, an inhibitor antibody having the following characteristics:
 a) specifically binds to said reporter enzyme,
 b) a dissociation constant less than or equal to about 125 nmolar, and
 c) specifically binds to said reporter enzyme in such a manner as to inhibit the enzymatic activity of said reporter enzyme by at least about 80%, and a water soluble conjugate of said target specific binding ligand and an anti-inhibitor antibody having the following characteristics:
 a) specifically binds to said reporter enzyme,
 b) a dissociation constant less than or equal to about 50 nmolar, and
 c) specifically binds to said reporter enzyme in such a manner that the enzymatic activity of said reporter enzyme is diminished by no more than 20%, and wherein said anti-inhibitor antibody prevents said inhibitor antibody from binding with said reporter enzyme.

12. The test kit of claim 11 wherein said reporter enzyme is immobilized on polymeric particles.

13. The test kit of claim 11 wherein either or both of said inhibitor antibody and said anti-inhibitor antibody are monoclonal antibodies.

14. The test kit of claim 11 wherein said reporter enzyme is horseradish peroxidase, said inhibitor antibody is monoclonal, has a dissociation constant of less than about 10 nmolar, and binds to said horseradish peroxidase in such a manner as to inhibit at least about 95% of the enzymatic activity of said horseradish peroxidase, and said anti-inhibitor antibody is monoclonal, has a dissociation constant greater than or equal to about 5 nmolar, and binds to said horseradish peroxidase in such a manner that the enzymatic activity of said horseradish peroxidase is diminished by no more than about 6%.

15. The kit of claim 11 wherein said target specific binding ligand is dphenylhydantoin, digoxin or phenobarbital; said immobilized receptor is an antibody which specifically binds to said target specific binding ligand; and wherein said water-soluble conjugate is formed from said anti-inhibitor antibody and said target specific binding ligand.

16. A dry analytical element comprising a porous spreading layer which contains an immobilized reporter enzyme, said element further comprising an immobilized receptor for a target specific binding ligand.

17. The element of claim 16 which further comprises a nonporous support having thereon, in order, one or more hydrophilic reagent layers, and said porous spreading layer.

18. The element of claim 16 wherein said reporter enzyme and receptor are immobilized on polymeric particles within said porous spreading layer.

19. A dry analytical element comprising a nonporous support having thereon, in order, one or more hydrophilic reagent layers, and a porous spreading layer, said element further comprising the following reagents wherein said reagents are located in the same or different reagent layers or in the spreading layer:
 1) an immobilized receptor for a target specific binding ligand,
 2) an immobilized reporter enzyme,
 3) an inhibitor antibody having the following characteristics:
  a) specifically binds to said reporter enzyme,
  b) a dissociation constant less than or equal to about 125 nmolar, and
  c) specifically binds to said reporter enzyme in such a manner as to inhibit the enzymatic activity of said reporter enzyme by at least about 80%, and
 4) a water soluble conjugate of said target specific binding ligand and an anti-inhibitor antibody having the following characteristics:
  a) specifically binds to said reporter enzyme,
  b) a dissociation constant less than or equal to about 50 nmolar, and
  c) specifically binds to said reporter enzyme in such a manner that the enzymatic activity of said reporter enzyme is diminished by no more than 20%, and wherein said anti-inhibitor antibody prevents said inhibitor antibody from binding with said reporter enzyme, provided that reagents 1) and 2) are kept separated from reagents 3) and 4) but are available for reaction when said element is used in an assay for said target specific binding ligand.

20. The element of claim 19 wherein reagents 1) and 2) are located in one or more layers different from the one or more layers containing reagents 3) and 4).

* * * * *